United States Patent [19]

Van Scott et al.

[11] 4,246,261

[45] Jan. 20, 1981

[54] ADDITIVES ENHANCING TOPICAL CORTICOSTEROID ACTION

[76] Inventors: Eugene J. Van Scott, 1138 Sewell La., Rydal, Pa. 19046; Ruey J. Yu, 4 Lindenwold Ave., Ambler, Pa. 19002

[21] Appl. No.: 65,332

[22] Filed: Aug. 9, 1979

[51] Int. Cl.³ .................... A01N 45/00; A61K 31/56
[52] U.S. Cl. ................................................ 424/240
[58] Field of Search ...................................... 424/240

[56] References Cited

U.S. PATENT DOCUMENTS

| | | | |
|---|---|---|---|
| 3,966,924 | 6/1976 | Fredriksson | 424/240 |
| 4,144,332 | 3/1979 | Voorhees | 424/240 |

OTHER PUBLICATIONS

Chem. Abstracts, vol. 86 (1977), Par. 96,018m.

Primary Examiner—Elbert L. Roberts
Attorney, Agent, or Firm—LeBlanc, Nolan, Shur & Nies

[57] ABSTRACT

Composition and method for enhancing therapeutic effects of corticosteroids to alleviate the symptoms of inflammation and exfoliation such as psoriasis, eczema, seborrheic dermatitis and other inflammatory skin conditions consisting of a solution, cream, lotion, ointment or gel containing as two active ingredients a corticosteroid and an additive are disclosed. The therapeutic composition may include one or more of corticosteroids typically present in a total amount of from 0.01 to 2 percent and one or more of hydroxy acids or related compounds present in a total amount from 0.01 to 2 percent by weight of the total composition. Topical application of the therapeutic composition in a solution, cream, lotion, gel or ointment has been found to achieve a substantial increase in antiinflammatory action of corticosteroids.

36 Claims, No Drawings

ADDITIVES ENHANCING TOPICAL CORTICOSTEROID ACTION

BACKGROUND OF THE INVENTION

Psoriasis is a chronic skin disease, and remains a disfiguring and disabling cutaneous impairment to millions of persons. The cause of psoriasis is unknown, and therefore prevention is impossible. Therapy has necessarily been empiric. One method of treatment employs the systemic use of antimitotic drugs such as methotrexate to induce remissions of the lesions. However, the use of methotrexate is accompanied by acute and chronic toxicity to tissues other than skin, and therefore, has been discredited. It is imperative then that other means of therapy by external delivery of drugs be found which either confine toxicity chiefly to the skin, or are nontoxic.

We have disclosed, in prior patents, several methods for treating psoriasis. For example, in our prior patent application entitled TREATMENT OF PSORIASIS, Ser. No. 371,516, filed June 19, 1973, now U.S. Pat. No. 3,904,766, we described the use of mechlorethamine hydrochloride ointment to treat psoriasis by topical application. In our prior patent application entitled TREATMENT OF PSORIASIS WITH N-METHYLDIETHANOLAMINE, Ser. No. 455,665, filed Mar. 28, 1974, now U.S. Pat. No. 3,920,840, we described our discovery that psoriatic conditions could also be successfully treated by utilizing one of the degradation products of mechlorethamine hydrochloride, N-methyldiethanolamine, a compound which is primarily antiinflammatory. In our prior patent application entitled TREATMENT OF PSORIASIS WITH 6-AMINONICOTINAMIDE AND THIONICOTINAMIDE, Ser. No. 601,411, filed Aug. 4, 1975, now U.S. Pat. No. 4,067,975, we described the use of 6-aminonicotinamide and thionicotinamide in the treatment of psoriasis by topical application. In our prior patent application entitled TREATMENT OF PSORIASIS WITH 6-SUBSTITUTED NICOTINAMIDES, 2-SUBSTITUTED PYRAZINAMIDES AND CLOSELY RELATED COMPOUNDS, Ser. No. 715,131, filed Aug. 17, 1976, now U.S. Pat. No. 4,141,977, we described the use of 6-aminonicotinamide derivatives and related compounds in the topical treatment of psoriasis.

Corticosteriods are well known antiinflammatory drugs which have been used for topical and systemic treatment of psoriasis. The results of using corticosteroids in topical treatment of psoriasis, however, have been variable and unpredictable. In some cases topical corticosteroids seemed to improve and eradicate the psoriatic lesions, but in other cases corticosteroids appear to be ineffective on topical administration. Drug resistance and rebound worsening are also common features when corticosteriods alone are used in the treatment of psoriasis.

Because psoriatic lesions consist of both erythema (red, inflamed) and thick scales we conceive the likelihood that anti-scaling drugs in corticosteroid preparations might facilitate the remission of psoriatic lesions.

In our prior patent application entitled TREATMENT OF ICHTHYOSIFORM DERMATOSES, Ser. No. 394,269, filed Sept. 4, 1973, now U.S. Pat. No. 3,879,537, we described and claimed the use of certain α-hydroxy acids, α-keto acids and related compounds for topical treatment of fish-scale like ichthyotic conditions in humans. In our patent application entitled TREATMENT OF DISTURBED KERATINIZATION, Ser. No. 445,231, filed Feb. 25, 1974, now U.S. Pat. No. 3,920,835, we described and claimed the use of these certain α-hydroxy acids α-keto acids and their derivatives for topical treatment of dandruff, acne, and palmar and plantar hyperkeratosis.

In our copending application Ser. No. 870,114, filed Jan. 17, 1978, the disclosure of which is hereby incorporated by reference, there is described the discovery that certain α-hydroxy acids and related compounds and reaction products of these compounds and certain organic amines or ammonium hydroxide are effective in the topical treatment of dry skin conditions.

Specifically, the acids and related compounds described were citric acid; glycolic acid; glucuronic acid; galacturonic acid; lactones, such as, glucuronolactone, and gluconolactone; α-hydroxybutyric acid; α-hydroxy-isobutyric acid; lactic acid; malic acid; mandelic acid; mucic acid; pyruvic acid; esters thereof, such as, methyl pyruvate and ethyl pyruvate; compounds related thereto, such as β-phenyllactic acid and β-phenylpyruvic acid; β-hydroxybutyric acid; saccharic acid, tartaric acid; and tartronic acid.

Basic reactants described therein included ammonium hydroxide, organic primary, secondary or tertiary amines, such as, alkylamines, alkanolamines, diamines, dialkyl amines, dialkanolamines, alkylalkanolamines, trialkylamines, trialkanolamines, dialkylalkanolamines, and alkyl dialkanolamines wherein the alkyl or alkanol substituent has from 1 to 8 carbon atoms.

In our copending patent application Ser. No. 948,489, filed Oct. 4, 1978, the disclosure of which is hereby incorporated by reference, we describe our discovery that certain free acids, related compounds and reaction products with certain organic or inorganic bases were effective upon topical application to alleviate the symptoms of actinic and nonactinic keratoses.

Specifically, the free acids and related compounds described were citric acid; glycolic acid; glucuronic acid; gluconic acid; galacturonic acid; glucoheptonic acid; lactones, such as, glucoheptono 1,4 lactone, gluconolactone, glucuronolactone; α-hydroxybutyric acid; α-hydroxyisobutyric acid; α-hydroxyisocaproic acid; α-hydroxyisovaleric acid; lactic acid; atrolactic acid; malic acid; mandelic acid; mucic acid; pyruvic acid; esters thereof, such as, methyl pyruvate, ethyl pyruvate, and isopropyl pyruvate; saccharic acid; its lactone, saccharic acid, 1,4-lactone; tartaric acid, tartronic acid; and related compounds, such as, β-hydroxybutyric acid; β-phenyl-lactic acid, β-phenylpyruvic acid.

The list of acids and related materials disclosed in our application Ser. No. 948,489, included the compounds identified application Ser. No. 870,114, and in addition gluconic acid, glucoheptonic acid, glucoheptono 1,4-lactone, α-hydroxy-isocaproic acid, α-hydroxyisovaleric acid, atrolactic acid, isopropyl pyruvate, and saccharic 1,4-lactone. This list then totals twenty-nine related compounds found to be effective against skin keratoses.

We also described in our patent application TREATMENT OF BODY ODOR AND DISTURBED KERATINIZATION, Ser. No. 703,188, filed July 7, 1976, now U.S. Pat. No. 4,053,630, the discovery that Cysteic acid, Cysteinesulfinic acid, and Homocysteic acid and metal chelates thereof are effective on topical application against certain skin conditions including acne, dandruff and ichthyosis. We further described in our copending application Ser. No. 949,536, filed Oct. 10, 1978, the disclosure of which is hereby incorporated by reference, that the above acids or reaction products with certain inorganic or organic bases were additionally effective against dry skin, actinic and nonactinic keratoses, warts, and palmar and plantar keratosis.

DESCRIPTION OF THE INVENTION

It has now been discovered that hydroxy acids and related compounds described in our patents and patent applications and additional related compounds, in small amounts greatly enhance the therapeutic efficacy of corticosteroids in topical treatment of psoriasis, eczema, seborrheic dermatitis and other inflammatory skin conditions.

The corticosteroids may include hydrocortisone, hydrocortisone-21-acetate, hydrocortisone 17-valerate, hydrocortisone-17-butyrate, triamcinolone acetonide and other synthetic or natural corticosteroids. The Therapeutic composition of this invention may include one or more of corticosteroids present in a total amount of from 0.01 to 2 percent and preferably from 0.02 to 0.5 percent by weight of the total composition.

The enhancing compounds of this invention include the following:

| (A) Hydroxymonocarboxylic Acids | (B) Hydroxy-di and Tricarboxylic Acids |
|---|---|
| 1. Glycolic Acid | 1. Malic Acid |
| 2. Glucuronic Acid | 2. Mucic Acid |
| 3. Galacturonic Acid | 3. Citric Acid |
| 4. Gluconic Acid | 4. Saccharic Acid |
| 5. Glucoheptonic Acid | 5. Tartaric Acid |
| 6. α-Hydroxybutyric Acid | 6. Tartronic Acid |
| 7. α-Hydroxyisobutyric Acid | 7. Isocitric Acid |
|  | 8. Dihydroxymaleic Acid |
| 8. α-Hydroxyisocaproic Acid | 9. Dihydroxytartaric Acid |
| 9. α-Hydroxyisovaleric Acid | 10. Dihydroxyfumaric Acid |
| 10. β-Hydroxybutyric Acid |  |
| 11. Lactic Acid |  |
| 12. β-Phenyllactic Acid |  |
| 13. Atrolactic Acid |  |
| 14. Mandelic Acid |  |
| 15. Galactonic Acid |  |
| 16. Pantoic Acid |  |
| 17. Glyceric Acid |  |

| (C) Ketoacids and Ketoesters | (D) Hydroxylactones |
|---|---|
| 1. Pyruvic Acid | 1. Gluconolactone |
| 2. Methyl Pyruvate | 2. Glucuronolactone |
| 3. Ethyl Pyruvate | 3. Glucoheptono Lactone |
| 4. Isopropyl Pyruvate | 4. Galactonolactone |
| 5. Benzoylformic Acid | 5. Saccharic Acid Lactone |
| 6. Methyl Benzoylformate | 6. Mucic Acid lactone |
| 7. Ethyl Benzoylformate | 7. Pantoyllactone |
| 8. β-Phenylpyruvic Acid |  |
| 9. β-Hydroxypyruvic Acid |  |
| 10. β-Hydroxypyruvic Acid Phosphate |  |

| (E) Alkene and Alkyne Dicarboxylic Acids and Esters Thereof | (F) Cysteic and Related Acids |
|---|---|
| 1. Maleic Acid | 1. Cysteic Acid |
| 2. Diethylmaleate | 2. Homocysteic Acid |
| 3. Dimethylmaleate | 3. Cysteinesulfinic Acid |
| 4. Acetylenedicarboxylic Acid |  |
| 5. Diethylacetylene dicarboxylate |  |
| 6. Dimethylacetylene dicarboxylate |  |

Accordingly, it is an object of this invention to provide a therapeutically active composition containing both corticosteroid and an hydroxy acid for topical application to alleviate the symptoms of psoriasis, eczema, seborrheic dermatitis and other inflammatory and hyperkeratotic skin conditions in humans.

It is another object of this invention to provide certain α-hydroxy acids which may be incorporated with corticosteroids in a pharmaceutically acceptable carrier which when topically applied to the lesions of psoriasis or other inflammatory and hyperkeratotic skin conditions will alleviate the symptoms thereof.

It is yet another object of this invention to provide a method for treating psoriasis or other inflammatory and hyperkeratotic skin conditions with a combination of certain acids, esters and lactones, and corticosteroids in a pharmaceutically acceptable carrier by topical application.

These and other objects will become readily apparent with reference to the following description.

PREPARATION OF THE THERAPEUTIC COMPOSITIONS

In order to prepare the compositions of this invention at least one of the aforementioned enhancing compounds of this invention and a corticosteroid are initially dissolved in a solvent such as water, ethanol or acetone. The solution thus prepared may then be admixed in a conventional manner with commonly available cream or ointment bases such as hydrophilic ointment or petrolatum. The concentration of the compound of this invention may range from 0.01 to 2 percent by weight of the total composition. The concentration of the corticosteroids ranges from 0.01 to 2 percent by weight of the total composition.

If desired, two or more of the aforementioned compounds and corticosteroids may be admixed as described above to form a composition of this invention. In this instance it is preferred that the total concentration of compounds of this invention not exceed about 1 percent by weight of the total composition.

The water, ethanol or acetone solvent used to initially dissolve the enhancing compounds and corticosteroids may have a concentration of from 1 to 10 percent by volume of the total composition. The preferred concentration thereof, however, is about 5 percent by volume of the total composition.

The therapeutic creams and ointments of this invention, prepared as described above, may be stored in cream or ointment jars.

The compounds of this invention and corticosteroids may also be incorporated in solution, gel or lotion form. A typical solution utilizing this invention comprises at least one of the above-named compounds dissolved directly in a warm mixture of sorbitan sesquioleate, polyoxyethylene (20) sorbitan monooleate, isopropyl myristate and propylene glycol in a volume ratio of preferably 20:20:40:20, respectively. The following substitutions of the ingredients may be made without compromising the therapeutic efficacy of the instant invention: sorbitan monooleate instead of sorbitan sesquioleate, polyoxyethylene (20) sorbitan monostearate instead of polyoxyethylene (20) sorbitan monooleate, isopropyl palmitate for isopropyl myristate and 1,3-butanediol for propylene glycol. The ratio of each vehicle may vary, however, the preferred concentration of sorbitan sesquioleate, polyoxyethylene (20) sorbitan monooleate or propylene glycol should not exceed 50 percent of the total composition. When solutions ae formulated according to this invention, the concentrations of both the enhancing compound and the corticosteroid are the same as described above.

The therapeutic solutions of this invention, prepared as described above, may be stored either in bottles having long droppers or in squeeze bottles attached with long nozzles. These therapeutic preparations are both convenient and efficacious in the topical treatment of hairy skin areas such as the scalp.

A typical gel preparation of this invention utilizes both the enhancing compound and the corticosteroid dissolved directly in a mixture of water, ethanol and propylene glycol in a volume ratio of 10:70:20 respectively. A gelling agent such as hydroxyethylcellulose, hydroxypropylcellulose or hydroxypropylmethylcellulose is then added to the mixture with agitation. The concentrations of the gelling agent may range from 0.1 to 2 percent by weight of the total composition.

A typical lotion containing both an enhancing compound and a corticosteroid may be prepared as follows: At least one of the compounds and one of the corticosteroids are dissolved in water or ethanol, and the solution is admixed with a lotion prepared from petrolatum, mineral oil, beeswax, isopropyl myristate and water with a surfactant such as sorbitan sesquioleate.

In an alternative way of formulating the therapeutic compositions, enhancing compounds and corticosteroids do not require any solvents for their dissolution prior to admixing with the lotion, cream or ointment. In this instance, fine powder forms of the compound and the corticosteroid are used, and they are mixed directly with a pharmaceutically acceptable base.

The following are illustrative examples of formulating compositions according to this invention. Although the examples utilize only certain α-hydroxy acids or related compounds of this invention with corticosteroids, the examples are not intended to be limited to the specific enhancing compound or corticosteroid named, but any member of the above-described classes of compounds or corticosteroids or combinations thereof could be substituted therefor within the scope of this invention.

The therapeutic composition may include one or more of hydroxy acids and related compounds present in a total amount of from 0.01 to 2 percent and preferably from 0.05 to 0.5 percent by weight of the total composition.

EXAMPLE 1

A water-in-oil cream may be prepared as follows:

| Part A: | |
| --- | --- |
| Sorbitan sesquioleate | 10 gm |
| Petrolatum | 15 gm |
| Mineral oil | 15 gm |
| Beeswax | 15 gm |
| Isopropylmyristate | 15 gm |
| Part B: | |
| Water | 30 ml |
| Magnesium hydroxide | 2 mg |

Heat both Part A and Part B to 80° C. Add Part B slowly to Part A with agitation. After the mixture is congealed, add 10% phosphoric acid 0.2 ml and aluminum chlorohydroxide 0.2 gm.

EXAMPLE 2

Hydrocortisone 0.2% in hydrophilic ointment is prepared as follows:

Hydrocortisone, USP microfine powder 0.2 gm is directly mixed with 99.8 gm of hydrophilic ointment USP. The mixing is continued until a uniform consistency is obtained.

EXAMPLE 3

Hydrocortisone 0.2% in water-in-oil cream is prepared as follows:

Hydrocortisone, USP microfine powder 0.2 gm is directly mixed with 99.8 gm of water-in-oil cream prepared according to Example 1. The mixing is continued until a uniform consistency is obtained.

EXAMPLE 4

Hydrocortisone 17-valerate 0.2% in hydrophilic ointment is prepared as follows:

Hydrocortisone 17-valerate powder 0.2 gm is directly mixed with 99.8 gm of hydrophilic ointment USP. The mixing is continued until a uniform consistency is obtained.

EXAMPLE 5

Hydrocortisone 17-valerate 0.2% in water-in-oil cream is prepared as follows:

Hydrocortisone 17-valerate powder 0.2 gm is directly mixed with 99.8 gm of water-in-oil cream prepared according to Example 1. The mixing is continued until a uniform consistency is obtained.

EXAMPLE 6

Hydrocortisone acetate 0.2% in hydrophilic ointment is prepared as follows:

Hydrocortisone acetate powder USP 0.2 gm is directly mixed with 99.8 gm of hydrophilic ointment USP. The mixing is continued until a uniform consistency is obtained.

EXAMPLE 7

Hydrocortisone acetate 0.2% in water-in-oil cream is prepared as follows:

Hydrocortisone acetate powder USP 0.2 gm is directly mixed with 99.8 gm of water-in-oil cream prepared according to Example 1. The mixing is continued until a uniform consistency is obtained.

EXAMPLE 8

Triamcinolone acetonide 0.02% in hydrophilic ointment is prepared as follows:

Triamcinolone acetonide 0.02 gm is directly mixed with 99.98 gm of hydrophilic ointment USP. The mixing is continued until a uniform consistency is obtained.

EXAMPLE 9

Triamcinolone acetonide 0.02% in water-in-oil cream is prepared as follows:

Triamcinolone acetonide 0.02 gm is directly mixed with 99.98 gm of water-in-oil cream prepared according to Example 1. The mixing is continued until a uniform consistency is obtained.

EXAMPLE 10

A hydrocortisone cream containing gluconolactone is formulated as follows:

Hydrocortisone, USP microfine powder 0.2 gm and gluconolactone powder 0.2 gm are directly mixed with 99.6 gm of hydrophilic ointment USP. The mixing is continued until a uniform consistency is obtained. The therapeutic composition thus prepared consists of 0.2% hydrocortisone and 0.2% gluconolactone in a water-washable cream.

EXAMPLE 11

A hydrocortisone cream containing mandelic acid is formulated as follows:

Hydrocortisone, USP microfine powder 0.2 gm and mandelic acid powder 0.2 gm are directly mixed with 99.6 gm of water-in-oil cream prepared according to Example 1. The mixing is continued until a uniform consistency is obtained. The therapeutic composition thus prepared consists of 0.2% hydrocortisone and 0.2% mandelic acid in a water-nonwashable cream.

EXAMPLE 12

A hydrocortisone cream containing atrolactic acid is formulated as follows:

Hydrocortisone, USP microfine powder 0.2 gm and atrolactic acid powder 0.2 gm are directly mixed with 99.6 gm of water-in-oil cream prepared according to Example 1. The mixing is continued until a uniform consistency is obtained. The therapeutic composition thus prepared consists of 0.2% hydrocortisone and 0.2% atrolactic acid in a water-nonwashable cream.

EXAMPLE 13

A hydrocortisone cream containing ethyl pyruvate is formulated as follows:

Hydrocortisone, USP microfine powder 0.2 gm and ethyl pyruvate 0.2 ml are directly mixed with 99.6 gm of water-in-oil cream prepared according to Example 1. The mixing is continued until a uniform consistency is obtained. The therapeutic composition thus prepared consists of 0.2% hydrocortisone and 0.2% ethyl pyruvate in a water-nonwashable cream.

EXAMPLE 14

A hydrocortisone cream containing pyruvic acid is formulated as follows:

Hydrocortisone, USP microfine powder 0.2 gm and pyruvic acid 0.2 ml are directly mixed with 99.6 gm of water-in-oil cream prepared according to Example 1. The mixing is continued until a uniform consistency is obtained. The therapeutic composition thus prepared consists of 0.2% hydrocortisone and 0.2% pyruvic acid in a water-nonwashable cream.

EXAMPLE 15

A hydrocortisone 17-valerate cream containing lactic acid is formulated as follows:

Hydrocortisone 17-valerate powder 0.2 gm and lactic acid, USP 0.2 ml are mixed with 99.6 gm of water-in-oil cream prepared according to Example 1. The mixing is continued until a uniform consistency is obtained. The therapeutic composition thus prepared consists of 0.2% hydrocortisone 17-valerate and 0.2% lactic acid in a water-nonwashable cream.

EXAMPLE 16

A hydrocortisone 17-valerate cream containing tartaric acid is formulated as follows:

Hydrocortisone 17-valerate powder 0.2 gm and tartaric acid 0.2 gm are directly mixed with 99.6 gm of water-in-oil cream prepared according to Example 1. The mixing is continued until a uniform consistency is obtained. The therapeutic composition thus prepared consists of 0.2% hydrocortisone 17-valerate and 0.2% tartaric acid in a water-nonwashable cream.

EXAMPLE 17

A hydrocortisone acetate cream containing maleic acid is formulated as follows:

Hydrocortisone acetate powder USP 0.2 gm and maleic acid powder 0.1 gm are directly mixed with 99.7 gm of water-in-oil cream prepared according to Example 1. The mixing is continued until a uniform consistency is obtained. The therapeutic composition thus prepared consists of 0.2% hydrocortisone acetate and 0.1% maleic acid in a water-nonwashable cream.

EXAMPLE 18

A hydrocortisone acetate cream containing diethylmaleate is formulated as follows:

Hydrocortisone acetate powder USP 0.2 gm and diethylmaleate 0.1 ml are directly mixed with 99.7 gm of water-in-oil cream prepared according to Example 1. The mixing is continued until a uniform consistency is obtained. The therapeutic composition thus prepared consists of 0.2% hydrocortisone acetate and 0.1% diethylmaleate in a water-nonwashable cream.

EXAMPLE 19

A triamcinolone acetonide cream containing mandelic acid is formulated as follows:

Triamcinolone acetonide 0.02 gm and mandelic acid 0.2 gm are directly mixed with 99.78 gm of water-in-oil cream prepared according to Example 1. The mixing is continued until a uniform consistency is obtained. The therapeutic composition thus prepared consists of 0.02% triamcinolone acetonide and 0.2% mandelic acid in a water-nonwashable cream.

EXAMPLE 20

A triamcinolone acetonide cream containing acetylene dicarboxylic acid is formulated as follows:

Triamcinolone acetonide 0.02 gm and acetylene dicarboxylic acid powder 0.1 gm are directly mixed with 99.88 gm of water-in-oil cream prepared according to Example 1. The mixing is continued until a uniform consistency is obtained. The therapeutic composition thus prepared consists of 0.02% triamcinolone acetonide and 0.1% acetylene dicarboxylic acid in a water-nonwashable cream.

EXAMPLE 21

A triamcinolone acetonide cream containing diethylacetylene dicarboxylate is formulated as follows:

Triamcinolone acetonide 0.2 gm and diethylacetylene dicarboxylate 0.1 ml are directly mixed with 99.88 gm of water-in-oil cream prepared according to Example 1. The mixing is continued until a uniform consistency is obtained. The therapeutic composition thus prepared consists of 0.02% triamcinolone acetonide and 0.1% diethylacetylene dicarboxylate in a water-nonwashable cream.

EXAMPLE 22

Hydrocortisone acetate solution containing ethyl pyruvate is prepared as follows:

Hydrocortisone acetate powder USP 0.2 gm and ethyl pyruvate 0.2 ml are dissolved in 10 gm of sorbitan sesquioleate, 10 gm of polyoxyethylene (20) sorbitan monooleate, 20 gm of mineral oil, 40 gm of isopropyl myristate and 20 gm of propylene glycol. The composition thus prepared may be stored in 2 ounce brown dropper bottles. The therapeutic solution which consists of 0.2% hydrocortisone acetate and 0.2% ethyl pyruvate is suitable for use involving the scalp area.

EXAMPLE 23

Hydrocortisone 17-valerate solution containing mandelic acid is prepared as follows:

Hydrocortisone 17-valerate powder 0.2 gm and mandelic acid 0.4 gm are dissolved in 10 gm of sorbitan sesquioleate, 10 gm of polyoxyethylene (20) sorbitan monooleate, 20 gm of mineral oil, 40 gm of isopropyl myristate and 20 gm of propylene glycol. The therapeutic solution thus formulated consists of 0.2% hydrocortisone 17-valerate and 0.4% mandelic acid, and is suitable for use involving the scalp area.

EXAMPLE 24

Hydrocortisone-21-acetate 0.2% and atrolactic acid 0.2% in water-in-oil cream is prepared as follows:

Hydrocortisone-21-acetate 0.2 gm and atrolactic acid 0.2 gm are directly mixed with 99.6 gm of the water-in-oil cream prepared according to Example 1. The mixing is continued until a uniform consistency is obtained.

EXAMPLE 25

Hydrocortisone-21-acetate 0.2% and gluconolactone 0.2% in in water-in-oil cream is prepared as follows:

Hydrocortisone-21-acetate 0.2 gm and gluconolactone 0.2 gm are directly mixed with 99.6 gm of the water-in-oil cream prepared according to Example 1. The mixing is continued until a uniform consistency is obtained.

EXAMPLE 26

Hydrocortisone 0.2% and acetic acid 0.2% in oil-in-water cream is prepared as follows:

Hydrocortisone, USP microfine powder 0.2 gm and glacial acetic acid 0.2 ml are directly mixed with 99.6 gm of hydrophilic ointment, USP. The mixing is continued until a uniform consistency is obtained.

EXAMPLE 27

Hydrocortisone 0.2% and ethyl acetate 0.2% in oil-in-water cream is prepared as follows:

Hydrocortisone, USP microfine powder 0.2 gm and ethyl acetate 0.2 ml are directly mixed with 99.6 gm of hydrophilic ointment, USP. The mixing is continued until a uniform consistency is obtained.

TEST RESULTS

In order to determine whether vehicle bases of different types such as oil-in-water or water-in-oil emulsion can affect the therapeutic efficacy of a corticosteroid, patients having psoriasis were selected for this study. Hydrocortisone 0.2%, hydrocortisone-21-acetate 0.2%, hydrocortisone-17-valerate 0.2% and triamcinolone acetonide 0.1% were prepared in (a) hydrophilic ointment (oil-in-water emulsion) (b) petrolatum (no water) and (c) water-in-oil emulsion according to the Examples described. These preparations were then topically tested on ten patients having psoriasis. After 10 days of three times daily topical administration it was discovered that all the corticosteroids in the water-in-oil emulsions showed the best improvement as compared to that in hydrophilic ointment or in petrolatum on all the patients tested. This result has been predicted from the fact that a water-in-oil emulsion (water nonwashable) can provide both the moisture and the occlusion that are beneficial in improving inflammatory and hyperkeratotic skin conditions. Hydrophilic ointment, on the other hand, can provide only moisture but no occlusion, and petrolatum affords only occlusion but not moisture.

It was therefore determined that water-in-oil emulsions should be chosen as the vehicle base in the study of an additive effect on therapeutic efficacy of a corticosteroid.

In order to determine whether a combination of a certain chemical agent with a corticosteroid could enhance the therapeutic action of a corticosteroid a total of more than 20 patients having psoriasis, a total of 9 patients having eczema and a total of 8 patients having seborrheic dermatitis were tested with various compositions as follows:

Therapeutic compositions of corticosteroids with or without an addition of certain chemical agents in water-in-oil cream prepared according to the Examples were topically administered to patients having psoriasis, eczema or seborrheic dermatitis. Formulations of corticosteroids containing either acetic acid or ethyl acetate were also included in the present clinical evaluation to establish whether an enhanced therapeutic action of corticosteroids by certain chemical agents of the instant invention is specific or nonspecific in nature.

Test areas in patients having psoriasis or eczema were kept to minimal size convenient for topical application: circles 4 cm in diameter demarcated with a plastic ring of that size inked on a stamp pad. The medicinal creams or ointments were topically applied by the patient in an amount (usually about 0.1 cubic millimeter) sufficient to cover the test site. Applications were made three times daily and without occlusive dressings. Test periods did not exceed two weeks and applications were discontinued at any time when resolution of the lesion on the test area was clinically judged to be complete.

The test results on psoriatic patients are summarized on the following table.

| Effects on Psoriasis of Topical Hydrocortisone With and Without Other Additives | | |
|---|---|---|
| Compositions | No. of Patients | Therapeutic Effectiveness |
| Hydrocortisone 0.2% alone | 14 | 2+ |
| With 0.2% acetic acid | 5 | 2+ |
| With 0.2% ethyl acetate | 5 | 2+ |
| With 0.2% atrolactic acid | 8 | 3+ |
| With 0.2% gluconolactone | 8 | 3+ |

-continued

Effects on Psoriasis of Topical Hydrocortisone With and Without Other Additives

| Compositions | No. of Patients | Therapeutic Effectiveness |
|---|---|---|
| With 0.2% glycolic acid | 6 | 3+ |
| With 0.2% pyruvic acid | 7 | 3+ |
| With 0.2% mandelic acid | 9 | 4+ |
| With 0.2% ethyl pyruvate | 8 | 4+ |
| With 0.2% tartaric acid | 5 | 3+ |

2+: Decrease of scale and erythema from lesions
3+: Disappearance of scale and erythema from lesions
4+: Restoration to normal looking skin As noted from the table, 0.2% hydrocortisone gave only 2+ improvement in all the patients tested. Addition of nonspecific chemicals such as acetic acid and ethyl acetate did not enhance the therapeutic effect of hydrocortisone. Whereas atrolactic acid, gluconolactone, glycolic acid, tartaric acid and pyruvic acid all substantially enhance the pharmacologic action of hydrocortisone, a combination of hydrocortisone with mandelic acid or ethyl pyruvate was found to be most effective in eradicating the lesions of psoriasis completely.

Under the same test conditions hydrocortisone-21-acetate alone at 0.2% could produce only a 2+ improvement on all 11 patients tested.

Effects on Psoriasis of Topical Hydrocortisone-21 Acetate With and Without Other Additives

| Compositions | Number of Patients | Therapeutic Effectiveness |
|---|---|---|
| Hydrocortisone acetate 0.2% alone | 11 | 2+ |
| With 0.2% atrolactic acid | 8 | 4+ |
| With 0.2% gluconolactone | 7 | 4+ |
| With 0.2% mandelic acid | 8 | 4+ |

As shown by the above table with the addition of 0.2% of atrolactic acid, gluconolactone or mandelic acid, hydrocortisone-21-acetate at the same concentration of 0.2% could now achieve a 4+ remission on all the psoriatic patients tested.

Under the same test circumstances hydrocortisone-17-valerate alone at 0.2% could achieve only a 3+ improvement on all 10 patients tested.

Effects on Psoriasis of Topical Hydrocortisone 17-Valerate With and Without Other Additives

| Compositions | Number of Patients | Therapeutic Effectiveness |
|---|---|---|
| Hydrocortisone 17-valerate 0.2% alone | 10 | 3+ |
| With 0.2% Glycolic acid | 7 | 4+ |
| With 0.2% Atrolactic acid | 7 | 4+ |
| With 0.2% Ethyl pyruvate | 6 | 4+ |
| With 0.2% Methyl pyruvate | 6 | 4+ |
| With 0.2% Gluconolactone | 6 | 4+ |
| With 0.2% Tartaric acid | 5 | 4+ |

As shown by the above table with the addition of 0.2% glycolic acid, atrolactic acid, ethyl pyruvate, methyl pyruvate, gluconolactone or tartaric acid, hydrocortisone-17-valerate at the same concentration of 0.2% could now achieve a 4+ maximal clearing on all the psoriatic patients tested.

Triamcinolone acetonide is one of the more potent corticosteroids in the topical treatment of psoriasis. However, triamcinolone acetonide alone at 0.02% could achieve only a 3+ improvement on all 12 psoriatic patients tested. As shown on the following table with the addition of 0.2% of ethyl pyruvate, methyl pyruvate, lactic acid, glycolic acid, mandelic acid, atrolactic acid, glucoheptono 1,4-lactone, glucuronic acid, tartaric acid or citric acid, triamcinolone acetonide at the same concentration of 0.02% could now achieve a 4+ maximal clearing on all the psoriatic patients tested.

Effects on Psoraisis of Topical Triamcinolone Acetonide with and without other Additives

| Compositions | Number of Patients | Therapeutic Effectiveness |
|---|---|---|
| Triamcinolone Acetonide 0.02% alone | 12 | 3+ |
| With 0.2% Ethyl pyruvate | 10 | 4+ |
| With 0.2% Methyl pyruvate | 9 | 4+ |
| With 0.2% Lactic acid | 6 | 4+ |
| With 0.2% Glycolic acid | 6 | 4+ |
| With 0.2% Mandelic acid | 6 | 4+ |
| With 0.2% Atrolactic acid | 6 | 4+ |
| With 0.2% Glucoheptono 1,4-lactone | 3 | 4+ |
| With 0.2% Glucuronic acid | 3 | 4+ |
| With 0.2% Tartaric acid | 4 | 4+ |
| With 0.2% Citric acid | 4 | 4+ |

In a topical treatment of eczema patients hydrocortisone alone at 0.5% could achieve only a 3+ improvement on all 9 eczema patients tested.

Effects on Eczema of Topical Hydrocortisone With and Without Other Additives

| Composition | Number of Patients | Therapeutic Effectiveness |
|---|---|---|
| Hydrocortisone 0.5% alone | 9 | 3+ |
| With 0.2% mandelic acid | 9 | 4+ |
| With 0.2% ethyl pyruvate | 7 | 4+ |

As shown by the above table with the addition of 0.2% of mandelic acid or ethyl pyruvate, hydrocortisone at the same concentration of 0.5% could attain a 4+ maximal clearing on all the eczema patients tested.

Psoriatic patients with scalp involvement and patients having seborrheic dermatitis on the scalp were instructed to apply topically a composition of corticosteroid alone on the right side of the scalp and a composition of corticosteroid containing other additives on the left side of the scalp. Applications were made two times daily and without any kind of additional treatment. Test periods did not exceed four weeks, and applications were discontinued at any time when resolution of the lesions on the scalp was clinically judged to be complete.

In most cases, the affected scalp of psoriatic patients and patients having seborrheic dermatitis became less flaky and less erythematous after a few days of topical treatment. The scaly and erythematous lesions ordinarily were substantially restored to normal appearing scalp after one to two weeks of treatment. The sites of the lesions, devoid of any dandruff and erythema, usually reached an improved state comparable to normal skin in the scalp within two to four weeks after initial treatment.

The test results on psoriatic patients with scalp involvement and patients having seborrheic dermatitis on the scalp are summarized in the following table.

| Effects of Topical Corticosteroids on Scalps of Psoriatic | | |
| --- | --- | --- |
| Composition | Number of Patients | Therapeutic Effectiveness |
| Hydrocortisone acetate 0.2% alone | 12 | 2+ |
| With 0.2% Mandelic acid | 9 | 3+ |
| With 0.4% Ethyl pyruvate | 8 | 3+ |
| Hydrocortisone 17-valerate 0.2% alone | 12 | 3+ |
| With 0.4% Mandelic acid | 12 | 4+ |
| With 0.2% Ethyl pyruvate | 9 | 4+ |

As shown by the above table, hydrocortisone acetate alone at 0.2% could achieve only a 2+ improvement on the scalps of psoritaric patients and on patients having seborrheic dermatitis. With the addition of 0.2% of mandelic acid or ethyl pyruvate, hydrocortisone acetate at the same concentration attained a 3+ remission.

Under the same test conditions, hydrocortisone-17-valerate alone at 0.2% could achieve only a 3+ improvement on the scalps of psoriatic patients and on patients having seborrheic dermatitis. With the addition of 0.2% mandelic acid or ethyl pyruvate, hydrocortisone-17-valerate at the same concentration of 0.2% achieved a 4+ or complete clearing of all patients tested.

In summary then we have discovered that certain hydroxy acids, esters, and lactones specifically enhance the anti-inflammatory activity of corticosteroids against inflammatory skin conditions. Test results show that the presence of a small amount of the acid or related compound will achieve a substantial improvement in the anti-inflammatory action of the corticosteroids tested.

The invention may be embodied in other specific forms without departing from the spirit or essential characteristics thereof. The present embodiments are therefore to be considered in all respects as illustrative and not restrictive, the scope of the invention being indicated by the appended claims, and all changes which come within the meaning and range of equivalency of the claims are therefore intended to be embraced herein.

What is claimed is:

1. A method for enhancing the antiinflammatory activity of a therapeutic composition including a corticosteroid compound selected from the group consisting of hydrocortisone, hydrocortisone-21-acetate, hydrocortisone 17-valerate, hydrocortisone-17-butyrate and triamcinolone acetonide in a pharmaceutically acceptable vehicle for topical application to inflamed areas of the human body comprising: admixing in said composition an effective amount of at least one member selected from the group consisting of:

| | |
| --- | --- |
| Glycolic Acid, | α-Hydroxyisocaproic Acid, |
| Glucuronic Acid, | α-Hydroxyisovaleric Acid, |
| Galacturonic Acid, | β-Hydroxybutyric Acid, |
| Gluconic Acid, | Lactic Acid, |
| Glucoheptonic Acid, | β-Phenyllactic Acid, |
| α-Hydroxybutyric Acid, | Atrolactic Acid, |
| α-Hydroxyisobutyric Acid, | Mandelic Acid, |
| | Galactonic Acid, |
| | Pantoic Acid, and |
| | Glyceric Acid. |

2. The method of claim 1 wherein said member is present in a concentration of 0.01 to 2 percent by weight of said composition.

3. The method of claim 1 wherein a plurality of said members are present in a total concentration of 0.01 to 2 percent by weight of said composition.

4. A method for enhancing the antiinflammatory activity of a therapeutic composition including a corticosteroid compound selected from the group consisting of hydrocortisone, hydrocortisone-21-acetate, hydrocortisone 17-valerate, hydrocortisone-17-butyrate and triamcinolone acetonide in a pharmaceutically acceptable vehicle for topical application to inflamed areas of the human body comprising: admixing in said composition an effective amount of at least one member selected from the group consisting of:

| | |
| --- | --- |
| Malic Acid, | Isocitric Acid, |
| Mucic Acid, | Dihydroxymaleic Acid, |
| Citric Acid, | Dihydroxtartaric Acid, |
| Saccharic Acid, | [Dihydroxyfumaric Acid]. |
| Tartaric Acid, | |
| Tartronic Acid. | |

5. The method of claim 4 wherein said member is present in a concentration of 0.01 to 2 percent by weight of said composition.

6. The method of claim 3 wherein a plurality of said members are present in a total concentration of 0.01 to 2 percent by weight of said composition.

7. A method for enhancing the antiinflammatory activity of a therapeutic composition including a corticosteroid compound selected from the group consisting of hydrocortisone, hydrocortisone-21-acetate, hydrocortisone 17-valerate, hydrocortisone-17-butyrate, and triamcinolone acetonide in a pharmaceutically acceptable vehicle for topical application to inflame areas of the human body comprising: admixing in said composition an effective amount of at least one member selected from the group consisting of:

| | |
| --- | --- |
| Pyruvic Acid, | Methyl Benzoylformate, |
| Methyl Pyruvate, | Ethyl Benzoylformate, |
| Ethyl Pyruvate, | β-Phenylpyruvic Acid, |
| Isopropyl Pyruvate, | β-Hydroxypyruvic Acid, |
| Benzoylformic Acid, and | β-Hydroxypyruvic Acid Phosphate. |

8. The method of claim 7 wherein said member is present in a concentration of 0.01 to 2 percent by weight of said composition.

9. The method of claim 7 wherein a plurality of said members are present in a total concentration of 0.01 to 2 percent by weight of said composition.

10. A method for enhancing the antiinflammatory activity of a therapeutic composition including a corticosteroid compound selected from the group consisting of hydrocortisone, hydrocortisone-21-acetate, hydrocortisone-17-valerate, hydrocortisone-17-butyrate, and triamcinolone acetonide in a pharmaceutically acceptable vehicle for topical application to inflamed areas of the human body comprising: admixing in said composition an effective amount of at least one member selected from the group consisting of:

| | |
| --- | --- |
| Gluconolactone, | Saccharic acid Lactone |
| Glucuronolactone, | Mucic acid lactone, |
| Glucoheptono Lactone, | Pantoyllactone, and |
| Galactonolactone. | |

11. The method of claim 10 wherein said member is present in a concentration of 0.01 to 2 percent by weight of said composition.

12. The method of claim 10 wherein a plurality of said members are present in a total concentration of 0.01 to 2 percent by weight of said composition.

13. A method for enhancing the antiinflammatory activity of a therapeutic composition including a corticosteroid compound selected from the group consisting of hydrocortisone, hydrocortisone-21-acetate, hydrocortisone 17-valerat hydrocortisone-17-butyrate and triamcinolone acetonide in a pharmaceutically acceptable vehicle for topical application to inflamed areas of the human body comprising: admixing in said composition an effective amount of at least one member selected from the group consisting of:

| | |
|---|---|
| Maleic Acid, | Diethylacetylene dicarboxylate, |
| Diethylmaleate, | Dimethylacetylene dicarboxylate, |
| Acetylenedicarboxylic Acid, and | Dimethylmaleate. |

14. The method of claim 13 wherein said member is present in a concentration of 0.01 to 2 percent by weight of said composition.

15. The method of claim 13 wherein a plurality of said members are present in a total concentration of 0.01 to 2 percent by weight of said composition.

16. A method for enhancing the antiinflammatory activity of a therapeutic composition including a corticosteroid compound selected from the group consisting of hydrocortisone, hydrocortisone-21-acetate, hydrocortisone 17-valerat hydrocortisone-17-butyrate and triamcinolone acetonide in a pharmaceutically acceptable vehicle for topical application to inflamed areas of the human body comprising: admixing in said composition an effective amount of at least one member selected from the group consisting of:

| | |
|---|---|
| Cysteic Acid, | Homocysteic Acid, and Cysteinesulfinic Acid. |

17. The method of claim 16 wherein said member is present in a concentration of 0.01 to 2 percent by weight of said composition.

18. The method of claim 16 wherein a plurality of said members are present in a total concentration of 0.01 to 2 percent by weight of said composition.

19. In an antiinflammatory composition for topical application to involved areas of the human body comprising an antiinflammatory effective amount of a corticosteroid in a pharmaceutically acceptable vehicle, the improvement comprising: an effective amount of at least one member selected from the group consisting of

| | |
|---|---|
| Glycolic Acid, | α-Hydroxybutyric Acid, |
| Glucuronic Acid, | α-Hydroxyisobutyric Acid, |
| Galacturonic Acid, | α-Hydroxyisocaproic Acid, |
| Gluconic Acid, | α-Hydroxyisovaleric Acid, |
| Glucoheptonic Acid, | β-Hydroxybutyric Acid, |
| Lactic Acid, | β-Phenyllactic Acid, |
| Atrolactic Acid, | Mandelic Acid, |
| Galactonic Acid, | Pantoic Acid, and |
| Glyceric Acid | |

Present in said composition to enhance the antiinflammatory activity of said corticosteroid.

20. The composition of claim 19 wherein said member is present in said composition in a concentration of from 0.01 to 2 percent by weight.

21. The composition of claim 19 wherein a plurality of said members are present in said composition in a total concentration of 0.01 to 2 percent by weight.

22. In an antiinflammatory composition for topical application to involved areas of the human body comprising an antiinflammatory effective amount of a corticosteroid in a pharmaceutically acceptable vehicle, the improvement comprising: an effective amount of at least one member selected from the group consisting of

| | |
|---|---|
| Malic Acid, | Isocitric Acid, |
| Mucic Acid, | Dihydroxymaleic Acid |
| Citric Acid, | Dihydroxytartaric Acid |
| Saccharic Acid, | [Dihydroxyfumaric Acid,] |
| Tartaric Acid, | and |
| Tartronic Acid | | present in said composition to enhance the antiinflammatory activity of said corticosteroid.

23. The composition of claim 22 wherein said member is present in said composition in a concentration of from 0.01 to 2 percent by weight.

24. A composition of claim 22 wherein a plurality of said members are present in said composition in a total concentration of 0.01 to 2 percent by weight.

25. In an antiinflammatory composition for topical application to involved areas of the human body comprising an antiinflammatory effective amount of a corticosteroid in a pharmaceutically acceptable vehicle, the improvement
comprising: an effective amount of at least one member selected from the group consisting of

| | |
|---|---|
| Pyruvic Acid, | Methyl Benzoylformate, |
| Methyl Pyruvate, | Ethyl Benzoylformate, |
| Ethyl Pyruvate, | β-Phenylpyruvic Acid, |
| Isopropyl Pyruvate, | β-Hydroxypyruvic Acid, |
| Benzoylformic Acid, and | β-Hydroxypyruvic Acid Phosphate | present in said composition to enhance the antiinflammatory activity of said corticosteroid.

26. The composition of claim 25 wherein said member is present in said composition in a concentration of from 0.01 to 2 percent by weight.

27. The composition of claim 25 wherein a plurality of said members are present in said composition in a total concentration of 0.01 to 2 percent by weight.

28. In an antiinflammatory composition for topical application to involved areas of the human body comprising an antiinflammatory effective amount of a corticosteroid in a pharmaceutically acceptable vehicle, the improvement comprising: an effective amount of at least one member selected from the group consisting of

| | |
|---|---|
| Gluconolactone, | Saccharic Acid, Lactone, |
| Glucuronolactone, | Mucic Acid Lactone, |
| Glucoheptono Lactone, | Pantoyllactone, and |
| Galactonolactone | | present in said composition to enhance the antiinflammatory activity of said corticosteroid.

29. The composition of claim 28 wherein said member is present in said composition in a concentration of from 0.01 to 2 percent by weight.

30. The composition of claim 28 wherein a plurality of said members are present in said composition in a total concentration of 0.01 to 2 percent by weight.

31. In an antiinflammatory composition for topical application to involved areas of the human body comprising an antiinflammatory effective amount of a corticosteroid in a pharmaceutically acceptable vehicle, the improvement comprising: an effective amount of at least one member selected from the group consisting of

| | |
|---|---|
| Maleic Acid, | Diethylacetylene dicarboxylate, |
| Diethylmaleate, | Dimethylacetylene dicarboxylate, |
| Dimethylmaleate, and | |
| Acetylenedicarboxylic Acid | | present in said composition to enhance the antiinflammatory activity of said corticosteroid.

32. The composition of claim 31 wherein said member is present in said composition in a concentration of from 0.01 to 2 percent by weight.

33. The composition of claim 31 wherein a plurality of said members are present in said composition in a total concentration of 0.01 to 2 percent by weight.

34. In an antiinflammatory composition for topical application to involved areas of the human body comprising an antiinflammatory effective amount of a corticosteroid in a pharmaceutically acceptable vehicle, the improvement comprising: an effective amount of at least one member selected from the group consisting of

| | |
|---|---|
| Cysteic Acid | Homocysteic Acid, and |
| | Cysteinesulfinic Acid | present in said composition to enhance the antiinflammatory activity of said corticosteroid.

35. The composition of claim 34 wherein said member is present in said composition in a concentration of from 0.01 to 2 percent by weight.

36. The composition of claim 34 wherein a plurality of said members are present in said composition in a total concentration of 0.01 to 2 percent by weight.

* * * * *